(12) United States Patent
Stihl

(10) Patent No.: US 6,749,563 B2
(45) Date of Patent: Jun. 15, 2004

(54) MEDICAL INSTRUMENT THAT CAN BE SPREAD, ESPECIALLY A LARYNGOSCOPE

(75) Inventor: Ewald Stihl, Geisingen (DE)

(73) Assignee: Karl Storz GmbH Co. KG (DE)

( * ) Notice: Subject to any disclaimer, the term of this patent is extended or adjusted under 35 U.S.C. 154(b) by 12 days.

(21) Appl. No.: 10/128,920

(22) Filed: Apr. 24, 2002

(65) Prior Publication Data

US 2002/0165433 A1 Nov. 7, 2002

Related U.S. Application Data

(63) Continuation of application No. PCT/EP00/10995, filed on Nov. 8, 2000.

(30) Foreign Application Priority Data

Nov. 11, 1999 (DE) .......................................... 199 54 442

(51) Int. Cl.[7] .............................................. A61B 1/267
(52) U.S. Cl. ........................ 600/196; 600/190; 600/193; 600/185; 600/224
(58) Field of Search .................................. 600/190, 195, 600/196, 193, 185, 219, 220, 184, 224, 225

(56) References Cited

U.S. PATENT DOCUMENTS

| | | | | |
|---|---|---|---|---|
| 3,841,317 A | * | 10/1974 | Awais | ........................ 600/203 |
| 5,868,668 A | | 2/1999 | Weiss | ........................ 600/224 |
| 6,024,696 A | * | 2/2000 | Hoftman et al. | ............ 600/224 |
| 6,354,995 B1 | * | 3/2002 | Hoftman et al. | ............ 600/219 |
| 6,364,832 B1 | * | 4/2002 | Propp | ........................ 600/220 |
| 6,432,048 B1 | * | 8/2002 | Francois | ...................... 600/220 |
| 2003/0069477 A1 | * | 4/2003 | Raisman et al. | ............ 600/220 |

FOREIGN PATENT DOCUMENTS

| | | |
|---|---|---|
| DE | 32 17 476 C2 | 12/1982 |
| WO | WO 98/33431 | 8/1998 |

* cited by examiner

*Primary Examiner*—Beverly M. Flanagan
(74) *Attorney, Agent, or Firm*—St. Onge Steward Johnston & Reens LLC

(57) ABSTRACT

The invention relates to a spreadable medical instrument, comprising a handle part and at least two spatula elements which are connected to said handle part and, via at least one adjusting mechanism, can be adjusted parallel or at an angle to one another between an initial position, in which the spatula elements rest against one another, and at least one working position. In the working position, the individual spatula elements are spaced at intervals so that they form lateral gaps at least in the distal area, and when the spatula elements are in a working position, these lateral gaps between the spatula elements can be covered almost entirely by swiveling flap elements. In order to produce a spreadable medical instrument that ensures that no soft tissues can penetrate between the spatula elements through the lateral gaps, the invention proposes that the adjusting flap elements of each side are secured on at least one of the spatula elements in such a way that, in the initial position of the spatula elements, they rest in a form-fitting manner on the outside of the other spatula part that is not equipped with the respective flap element.

7 Claims, 3 Drawing Sheets

MEDICAL INSTRUMENT THAT CAN BE SPREAD, ESPECIALLY A LARYNGOSCOPE

This application is a continuation of pending International Application PCT/EP00/10995 filed on Nov. 8, 2000, which designates the United States and claims priority of German Application 199 54 442.5 filed on Nov. 11, 1999.

FIELD OF THE INVENTION

The invention relates to a spreadable medical instrument, comprising a handle part and at least two spatula elements which are connected to said handle part and, via at least one adjusting mechanism, can be adjusted parallel or at an angle to one another between an initial position, in which the spatula elements rest against one another, and at least one working position. In the working position, the individual spatula elements are spaced at intervals so that they form lateral gaps at least in the distal area, and when the spatula elements are in a working position, these lateral gaps between the spatula elements can be covered almost entirely by swiveling flap elements.

BACKGROUND OF THE INVENTION

Laryngoscopes are used particularly for direct instrumental inspection of the larynx as well as for endolaryngeal surgical interventions. Laryngoscopes are basically broken down into fixed and spreadable laryngoscopes. With a fixed laryngoscope, the spatula part connected to the handle part takes the shape of a tube, which is closed or possibly unilaterally slit, hollow and basically cylindrical, and which has a constant lumen for the introduction of appropriate medical instruments. Fixed laryngoscopes have the disadvantage that, on the one hand, the lumen cannot be enlarged on demand and, on the other hand, it is nevertheless necessary to introduce the laryngoscope with its nonadjustable lumen into the mouth and pharynx of the intubated and anaesthetized patient.

These difficulties can be avoided by employing spreadable laryngoscopes. These laryngoscopes feature a spatula part connected to a handle part and consisting of at least two spatula elements, which can be adjusted in relation to one another, and whose lumen can be adjusted between an initial position for the introduction and removal of the laryngoscope—with the spatula elements as close to each other as possible, and a working position, in which the individual spatula elements are adjusted parallel and/or at an angle to each other. When adjusting the individual spatula elements parallel and/or at an angle to each other, gaps are created between the individual spatula elements, at least in the spatula elements' distal area. Yet the configuration of this gap has the disadvantage that soft parts, such as the cheek or tongue, can pass through these lateral gaps into the laryngoscope's interior space, exposing them to possible injury, while also considerably reducing the surgeon's working space.

In order to prevent soft parts from penetrating into a spreadable medical instrument during surgery, it standard practice to keep the gap closed by pressing an additional spatula from the instrument's inner side. It has also proved helpful to roughen the spatula elements' outer surface, which prevents the tongue, for instance, from slipping laterally. The use of an additional spatula considerably reduces the free lumen at the surgeon's disposal and also necessitates the help of an assistant. The spatula elements' roughened outer surface also makes it difficult to clean the medical instrument so that, to some extent, this model too can be considered disadvantageous.

A typical spreadable medical instrument is known from U.S. Pat. No. 5,868,668 A. With this known medical instrument, the flap parts that cover the lateral gap are connected to the handle part so as to swivel and occupy the spatula elements' initial position between these spatula elements. Only after the spatula elements have been spread into a first open position, can the flap elements be swiveled into the position where they cover the lateral gap, at least partially. Yet since the flap elements cannot be actuated during the spatula elements' initial opening, it is possible for tissue to slip in between the spatula elements and to reduce the surgeon's working space. This known instrument has the further disadvantage of forcing the surgeon to swivel the flap elements manually by further spreading the spatula elements and, in addition, of requiring that the spatula elements be kept open by continuous manual intervention.

WO 98/33431 also demonstrated how to cover the spatula elements, which can be adjusted to each other, with a sleeve made of elastic material, which stretches when the individual spatula elements are being adjusted to each other, thus closing the lateral gap between the spatula elements. This method for closing the lateral gap has the disadvantage that, thanks to the stretchable, elastic material that envelops the spatula elements, the effort needed to adjust the spatula elements to each other, on top of the pressure exerted by the surrounding tissue, is considerably increased and thus the spatula elements are permanently under pressure to snap back into the closing (initial) position. In addition, there is the risk that during the introduction of the surgical instruments as well as during laser surgery, the elastic material becomes damaged, thus canceling, or at least reducing, its protective effect.

Based on this state-of-the-art, it is the purpose of the invention to develop a spreadable medical instrument of the initially described type, in such a way that its easy application, in a simple and reliable manner, prevents soft tissue from entering through the lateral gap between the spread spatula elements.

The solution provided by this invention is characterized in that the swiveling flap elements of each side are each fixed to at least one spatula part in such a way that, in the initial position of the spatula elements, they rest in a form-fitting manner on the outside of the other spatula part that is not equipped with the respective flap element.

Securing the flap elements of each side to at least one spatula part each, as provided by this invention, ensures that the flap elements are ready from the onset of the opening movement of the spatula elements and immediately close the emerging lateral gap without requiring a separate actuation of the flap elements. Since, in the initial position, the flap elements rest in a form-fitting manner on the spatula elements, and since the spreading spatula elements swivel them into a position where they cover the gap, an instrument designed in this manner offers the surgeon, at all times, an open cross-section in which to operate.

The form-fitting attachment of the flap elements to the spatula elements facilitates the introduction and removal of the spreadable medical instrument in its initial position, since the medical instrument's circumference, increases only slightly in comparison to an instrument without flap elements, but still is considerably smaller than the circumference of a fixed endoscope with a comparable operating cross-section.

Based on a practical embodiment of the invention, it is further proposed that the flap elements swivel automatically over the spatula elements that are adjustable to each other.

This automatic closing of the lateral gap does not require additional manipulations or other measures, so that the surgeon has greater freedom of movement.

Another advantageous proposal is to fix the flap elements to the spatula elements in such a way that they can be detached, which further simplifies cleaning.

A preferred embodiment of a spreadable medical instrument with two spatula elements that can be adjusted to one another proposes that one spatula element be secured rigidly to the handle part while the other spatula element is connected to the handle part in an adjustable manner, parallel and at an angle to the secured spatula element, and one swiveling flap element is secured to each longitudinal side of the rigidly secured spatula element. The configuration with one rigidly secured and one adjustable spatula element enables an especially simple adjustment mechanism to adjust the position of the spatula elements in relation to each other.

The operation of the flap elements can be further simplified by spring-loading them in their initial position next to the spatula elements. This ensures that the flap elements immediately return to their position interlocking with the spatula elements as soon as the spatula elements are closed again.

The height of the swiveling flap elements of this invention is calculated in such a manner that at least part of each flap element in the working position of the spatula elements fits close to the outer surface of the spatula element which is not equipped with this particular flap element. This prevents the flap elements from tilting inside between the spatula elements and blocking any readjustment of the spatula elements to their initial position.

In addition, the invention proposes that the outer surfaces of the spatula elements and/or the flap elements be smooth. Because of the use of flap elements, which close the lateral gap, it becomes unnecessary to roughen the outer surfaces, so that such a spreadable medical instrument can be easily and thoroughly cleaned.

Finally, the invention proposes that the spreadable medical instrument be a laryngoscope.

BRIEF DESCRIPTION OF THE DRAWINGS

The following description of the corresponding drawing reveals additional characteristics and advantages, showing, only as an example, a model of the invention of a spreadable medical instrument, designed as a laryngoscope. The illustrations are as follows.

DETAILED DESCRIPTION OF THE DRAWINGS

Figure 1:
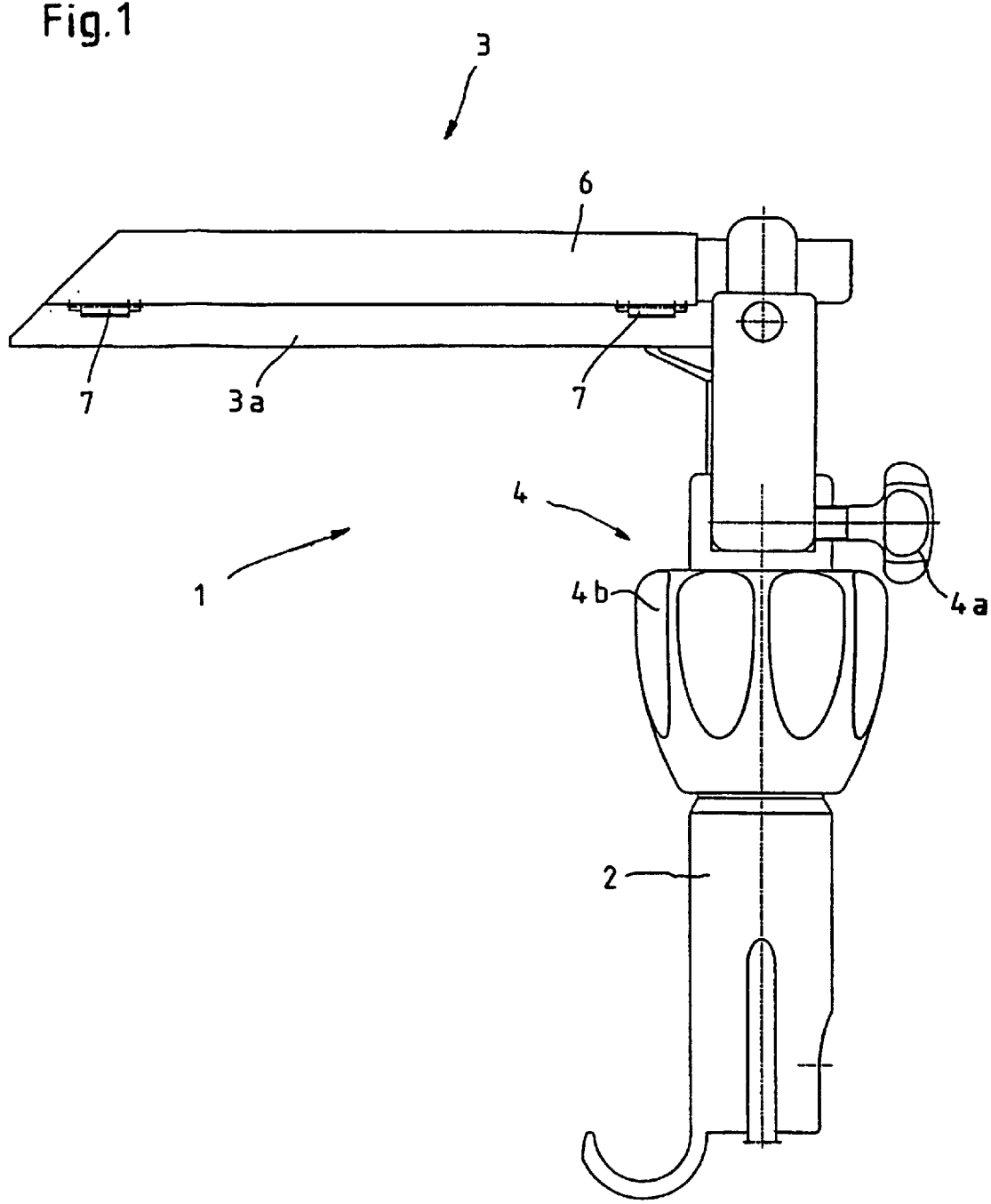
FIG. 1 Lateral view of a laryngoscope based on the invention, in its initial position.

FIG. 1 shows a lateral view of a laryngoscope 1, which essentially consists of a handle part 2 and a spatula part 3. The depicted laryngoscope 1 is a spreadable laryngoscope 1 whose spatula part 3 consists of a solidly fixed spatula element 3a and a spatula element 3b, which, in comparison to the rigidly secured spatula element 3a, can be adjusted. Spatula element 3a and spatula element 3b are adjusted to each other by means of an adjustment mechanism 4 consisting of two adjusting screws 4a and 4b.

Figure 2:
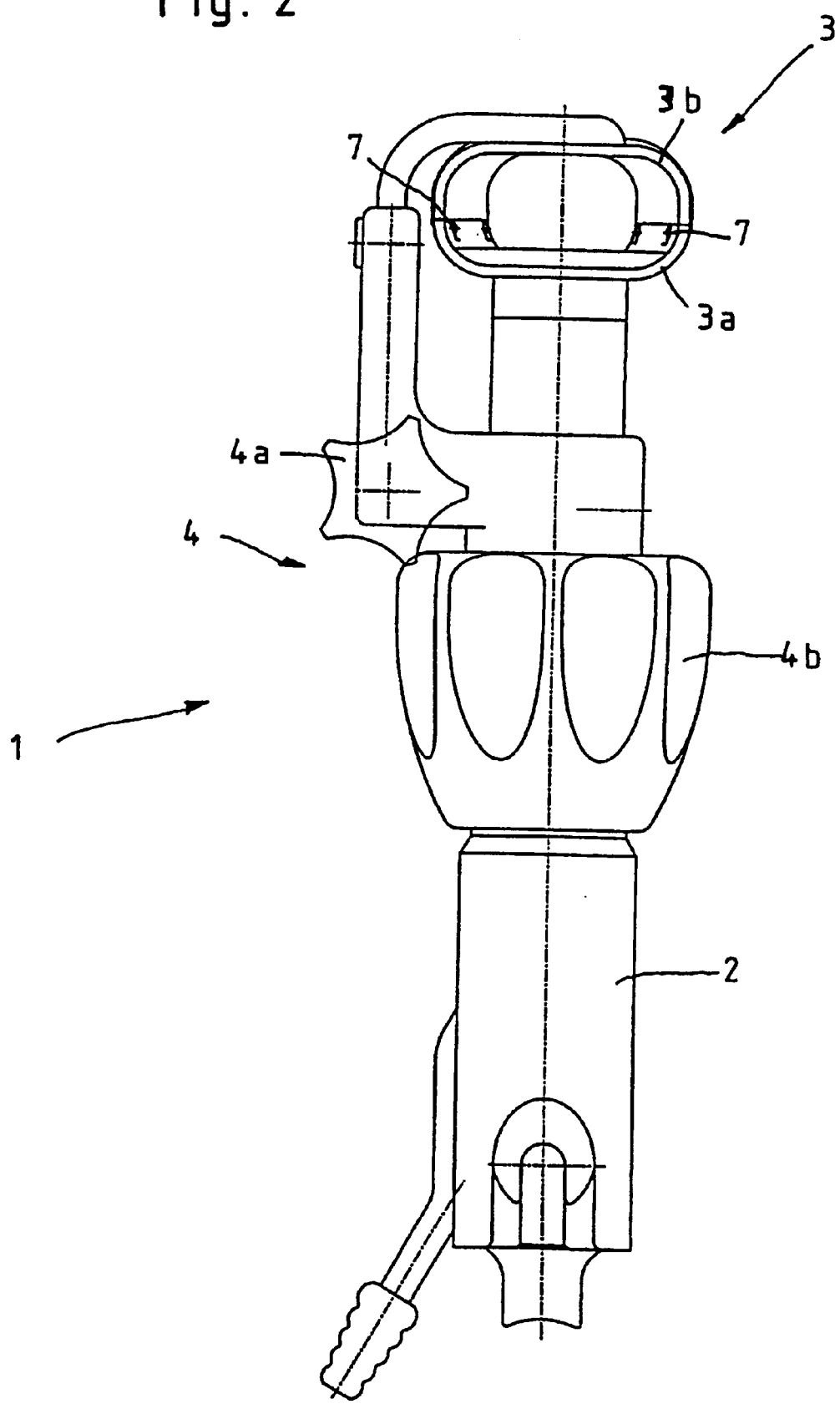
FIG. 2 View of a laryngoscope according to FIG. 1, from behind.

FIGS. 1 and 2 show a laryngoscope in the initial position, with the spatula elements 3a and 3b lying as closely together as possible, in order to enable the smoothest and easiest possible insertion or removal of the laryngoscope's spatula part 3 into or out of a patient's mouth and throat, respectively. The remaining lumen of the spatula part 3 in the initial position suffices to determine the position of the laryngoscope 1 in the patient's throat with an attached light source.

Figure 3:
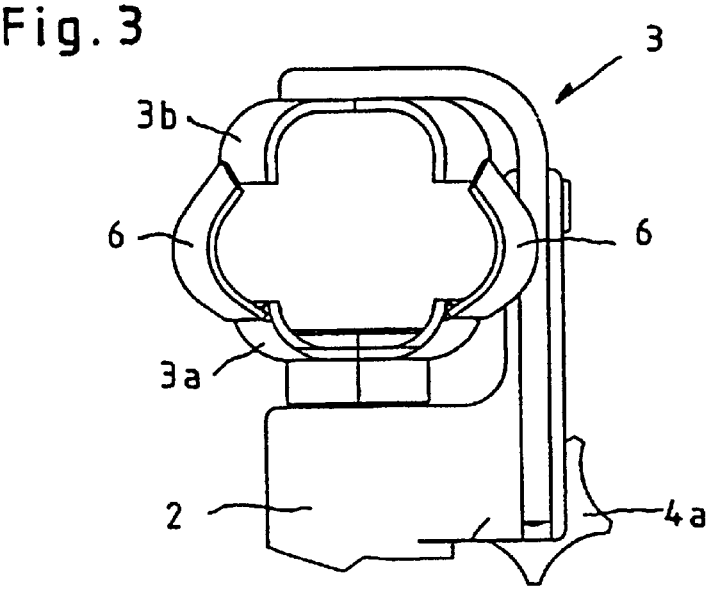
FIG. 3 Section of the laryngoscope's a frontal view according to FIGS. 1 and 2, but showing a working position.

In order to prevent soft parts, such as, for example, the cheek or tongue, from penetrating into the lateral gap 5 emerging between the spatula elements 3a and 3b as shown in FIGS. 1 to 3, in the laryngoscope's 1 interior, risking injury to these soft parts and considerably reducing the lumen for the surgeon, the illustrated laryngoscope 1 features swiveling flap elements 6 at the rigidly secured spatula element 3a, which, in working position, cover the gap 5 for the most part.

For this design, the swiveling flap elements 6 are attached to the rigidly secured spatula element 3a by means of hinges 7 and are, in the initial position of the spatula elements 3a and 3b, essentially form-fittingly close to the outside of the adjustable spatula element 3b so that the circumference of spatula part 3 is only slightly enlarged by the flap elements 6.

Figure 4:
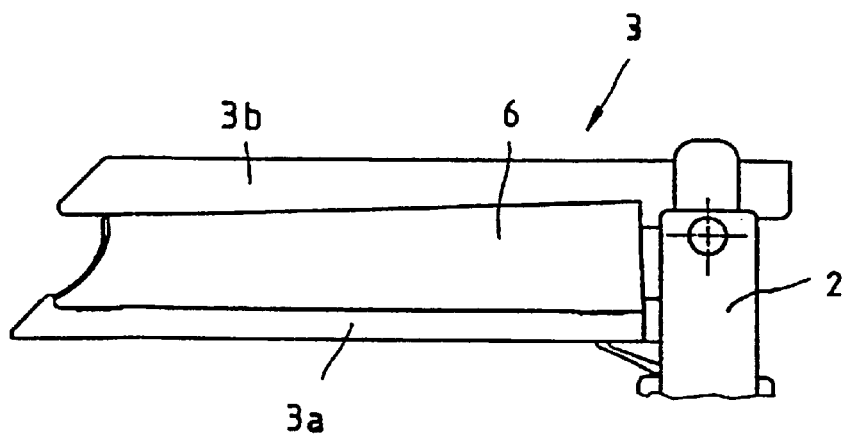
FIG. 4 Schematic lateral view of the spatula elements in working position with parallel adjusted spatula elements.
Figure 5:
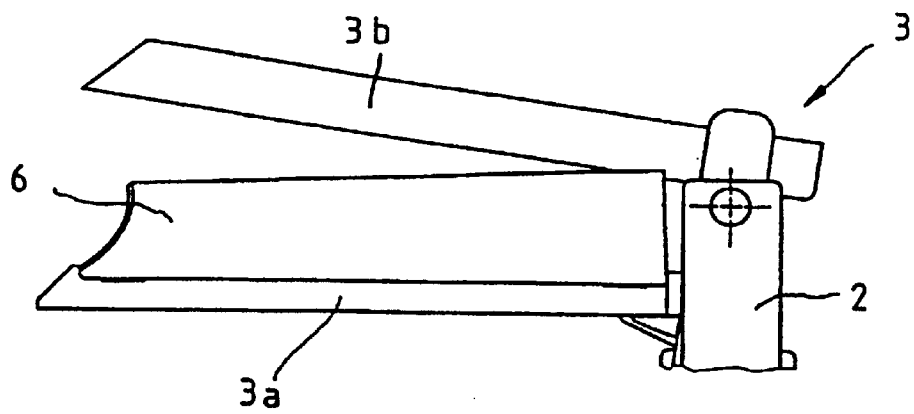
FIG. 5 Schematic lateral view according to FIG. 4, but with the spatula elements adjusted at an angle to each other.

After the insertion of the spatula part 3 of laryngoscope 1 into the patient's throat, the spatula elements 3a and 3b are adjusted to each other, either parallel as in FIGS. 3 and 4, and/or at an angle as in FIG. 5, in order to enlarge the lumen of spatula part 3 to create enough space and room in the distal area to perform surgery. When the spatula elements 3a and 3b are moved apart, the flap elements 6 are automatically pushed out from the initial position shown in FIGS. 1 and 2 in such a way that they close the lateral gap 5 between the spatula elements 3a and 3b in the working position as shown in FIG. 3.

In addition to the depicted configuration in which the flap elements 6 are attached to only one spatula part, i.e. to the rigidly secured spatula element 3a, it is, of course, also possible to attach the flap elements 6 to the flexible spatula element 3b or to one side of element 3a and to the other side of element 3b, with a joint.

FIG. 5 shows the spatula part 3 in a working position in which the spatula elements have been, in addition, pivoted at an angle to each other. In order to guarantee a smooth operation of a laryngoscope 1 in this configuration, one has to make sure that the height of the individual flap elements 6 is calculated so that at least part of each flap element 6 in the working position of the spatula elements 3a, 3b fits close to the outer surface of the spatula element 3b, i.e. the one that is not equipped with this particular flap element 6. Otherwise, the flap elements 6 could tilt inside between the spatula elements 3a and 3b, which would lead to complications when adjusting the spatula elements 3a and 3b to the initial position.

After the operation, the spatula elements 3a and 3b are restored to the initial position, with the flap elements 6 automatically returning to their form-fitting position close to the outside of spatula element 3b. The return of the flap elements 6 can be supported by restraining them with a spring in their initial position next to spatula element 3b.

It is characteristic for a spreadable medical instrument of this design that the swiveling flap elements 6, which are attached to at least one of the spatula elements 3a, 3b, close the gap between the spatula elements 3a and 3b so tightly in working position that they eliminate the danger of soft parts, such as e.g. the cheek or the tongue, getting in between the spatula elements 3a and 3b. Because of this safe closure of the gap 5, the outer surfaces of the spatula elements 3a and 3b can be as smooth as possible since it is no longer necessary that the tongue be held back by a roughened surface of these parts, as known in practice. A laryngoscope 1 of this design can therefore be cleaned easily and thoroughly.

In addition to the described use of the spreadable medical instrument as a laryngoscope, its configuration can also be used for a variety of endoscopic applications, such as, e.g., for spine or plastic surgery, during which soft parts must be prevented from entering the spreadable endoscopic access area. The spreadable access area has the advantage of providing a large distal work area, combined with a comparatively small circumference in the initial position, during insertion or removal.

What is claimed is:

1. Spreadable medical instrument, comprising a handle part and at least two spatula elements which are connected to said handle part and, via at least one adjusting mechanism, can be adjusted parallel or at an angle to one another between an initial position, in which the spatula elements rest against one another defining a remaining lumen between one another, and at least one working position, whereby, in the working position, the individual spatula elements are spaced at intervals so that they form lateral gaps at least at a distal end, and when the spatula elements are in the working position, the lateral gaps can be covered almost entirely by swiveling flap elements, whereby the swiveling flap elements of each side are each pivotably fixed to a spatula element in such a way that, in the initial position of the spatula elements, the swiveling flap elements rest in a form-fitting manner on the outside of the respective spatula element that is not equipped with the respective flap element characterized in that the flap elements swivel automatically over the spatula elements that are adjustable with respect to each other.

2. Spreadable medical instrument in accordance with claim 1, characterized in that the flap elements are secured to the spatula elements in such a way that they can be detached.

3. Spreadable medical instrument in accordance with claim 2, characterized in that one spatula element is rigidly connected with the handle part and the other spatula element is connected adjustably with the handle part parallel and at an angle, and that in each case one swiveling flap element is arranged on one longitudinal side of the rigidly connected spatula element.

4. Spreadable medical instrument in accordance with claim 3, characterized in that the swiveling flap elements are spring-loaded in their initial position next to the spatula elements.

5. Spreadable medical instrument in accordance with claim 4, characterized in that the height of the swiveling flap elements is calculated in such a manner that at least part of each flap element in the working position of the spatula elements fits close to the outer surface of the spatula element which is not equipped with this particular flap element.

6. Spreadable medical instrument in accordance with claim 5, characterized in that the outer surfaces of the spatula elements and/or the flap elements are smooth.

7. Spreadable medical instrument in accordance with claim 6, characterized in that the instrument is a laryngoscope.

* * * * *

UNITED STATES PATENT AND TRADEMARK OFFICE
CERTIFICATE OF CORRECTION

PATENT NO. : 6,749,563 B2
DATED : June 15, 2004
INVENTOR(S) : Ewald Stihl

It is certified that error appears in the above-identified patent and that said Letters Patent is hereby corrected as shown below:

<u>Title page,</u>
Item [73], should read as follows:  -- Assignee: Karl Storz GmbH & Co. KG --

Signed and Sealed this

Seventh Day of September, 2004

JON W. DUDAS
*Director of the United States Patent and Trademark Office*